United States Patent [19]

Schwartz

[11] 4,098,278
[45] Jul. 4, 1978

[54] DERMATOME APPARATUS AND METHOD

[76] Inventor: Boris Schwartz, 400 Park Ave., Paterson, N.J. 07504

[21] Appl. No.: 758,425

[22] Filed: Jan. 11, 1977

[51] Int. Cl.² ............................................. A61B 17/32
[52] U.S. Cl. ................................................. 128/305.5
[58] Field of Search ................ 30/280, 282; 128/305.5

[56] References Cited

U.S. PATENT DOCUMENTS

| | | | |
|---|---|---|---|
| 2,442,436 | 6/1948 | Reese | 128/305.5 |
| 2,611,952 | 9/1952 | Chambers | 30/280 X |
| 3,428,045 | 2/1969 | Kratzsch | 128/305.5 |
| 3,670,734 | 6/1972 | Hardy, Jr. | 128/305.5 |

*Primary Examiner*—Robert W. Michell
*Assistant Examiner*—Arthur S. Rose
*Attorney, Agent, or Firm*—Ralph R. Roberts

[57] ABSTRACT

This invention pertains to an improved apparatus and method in which an adhesive strip of material having a given width and thickness is used with a razor blade-type of cutter and a transverse guide. The apparatus is of inexpensive construction adapted for discarding after a one-time use. The adhesive is applied to a plastic strip of given thickness and width. One end of this tape is provided with an entering and grasping tongue or end. A sliding guide member is provided and carries a razor blade-type knife which is manually moved along transverse of this guide. A guideway is formed in this guide member and forming one side of this guideway is the cutting edge of the knife or blade. The blade may be fixed or adjusted within close limits so that the thickness of skin removed is between 5 and 20 thousandths of an inch in thickness. The width of the removed skin is the width of the adhesive strip, which may be as much as 3 inches.

11 Claims, 15 Drawing Figures

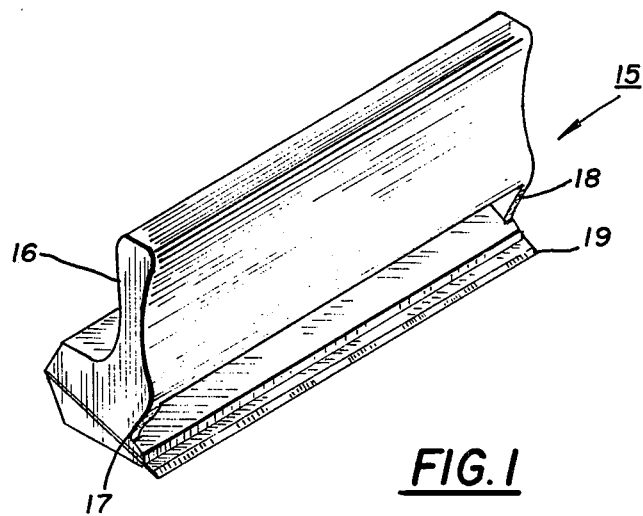
FIG. 1
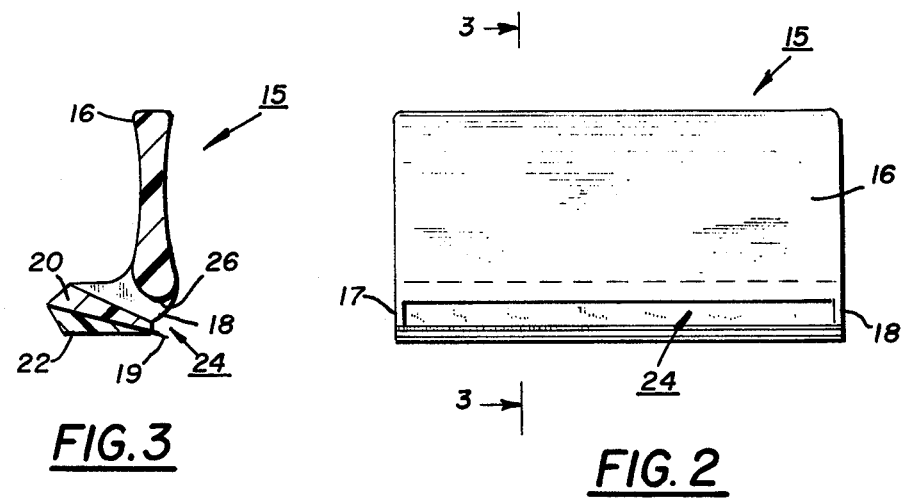
FIG. 3
FIG. 2
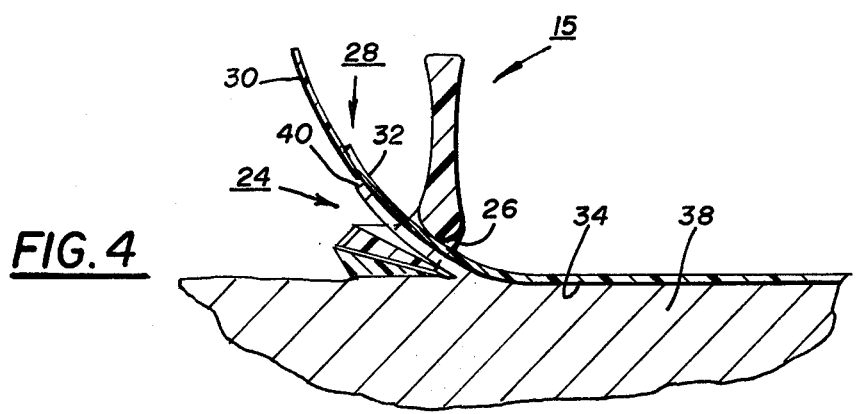
FIG. 4

DERMATOME APPARATUS AND METHOD

BACKGROUND OF THE INVENTION

1. Field of the Invention

With reference to the classification of art as established in the United States Patent and Trademark Office the present invention is found in the general Class entitled, "Surgery" (Class 128) and in the subclass thereunder entitled, "dermatome" (subclass 305.5).

2. Description of the Prior Art

The transfer of skin from one part of a person's body to a damaged portion is a well known and accepted procedure. Skin for such transfer is usually only a few thousandths of an inch in thickness. For example, thin units of skin in thicknesses of five- to twenty-thousandths of an inch are and have been satisfactorily used. Several patents directed toward a mechanical assist for the removal of skin have issued. Among these patents some have been commercially produced and are used in hospitals. A powered knife with an adjustable thickness guide is shown in U.S. Pat. No. 1,594,613 to HAGEN as issued on Aug. 3, 1926. A hand-powered knife with curved support and collecting unit is shown in U.S. Pat. No. 2,288,709 to HOOD as issued on July 7, 1942. A similar and improved device is seen in U.S. Pat. No. 2,400,336 to BISHOP as issued on May 14, 1946.

An elaborate device requiring vacuum is shown in U.S. Pat. No. 2,590,299. This retains the separated skin on a drum. In association with this drum, a powered knife blade is employed. This equipment is rather awkward to use, requires extensive preparation for sterilization and is expensive to procure and maintain. A vacuum source and usually pressurized air is required.

The invention, to be hereinafter more fully disclosed, contemplates an inexpensive apparatus that may be for one-time use and then discarded. No power or assist in the form of vacuum or pressurized air is contemplated. The dermatome apparatus is useable in or away from the hospital and requires no assist for manipulating.

SUMMARY OF THE INVENTION

This invention may be summarized in part with reference to its objects.

It is an object of this invention to provide a simple dermatome employing an adhesively backed plastic strip and a cutting blade carried by and on a guide member which is moved under and along the plastic strip as the skin is cut.

It is a further object of this invention to provide an inexpensive one-time use dermatome apparatus for hospital or ambulance use. This apparatus requires no electric, pneumatic or vacuum assists.

In one embodiment is shown a dermatome apparatus in which the blade is fixed as to a space between the cutting blade edge and a curved guide surface. The thickness of the plastic strip and the residual space to the cutting edge of the blade govern the resulting thickness of skin removed. The width of the plastic strip as and when the cut skin is severed by the reciprocating blade establishes and governs the width of the skin removed.

In alternate embodiments are shown an adjustable blade and a guide for the plastic strip in which the blade carrier is reciprocated in a desired plane and spacing with the plastic strip having a smooth outer surface on which the blade carrier is reciprocated, this strip on its other side having an adhesive coating.

In brief, this invention provides a dermatome apparatus which is furnished in a standard sterile condition in an inexpensive paper cover. One or more plastic strips are provided in this package. Each strip has a guide and a grasp end and adjacent this end is an extent of given width and length. This portion is provided with an adhesive on one surface. This adhesive is applied to a plastic strip of given thickness and until time of use with a release sheet applied thereto.

The cutting blade is of metal and is very similar to a razor blade in configuration except that it may be as long as five inches when the strip of skin to be removed is three inches wide. The blade is carried in a throw-away, plastic member which is formed with a guideway into which the blade extends a determined distance. This member has a grasping portion by which the member and the secured blade are moved back and forth in and with a reciprocating motion to cut the skin which is adhered to the plastic strip. The space in the guideway, the thickness of the plastic strip and adhesive and the projection of the blade into this space determines the resulting thickness of removed skin.

In alternate embodiments are shown modifications of the throw-away apparatus for removing portions of skin of a determined thickness and extent.

In addition to the above summary the following disclosure is detailed to insure adequacy and aid in understanding of the invention. This disclosure, however, is not intended to cover each new concept no matter how it may later be disguised by variations in form or additions of further improvements. For this reason there has been chosen a specific embodiment of the dermatome apparatus in its simplest arrangement as adopted for use for removing an outer portion of skin. This specific embodiment and alternate embodiments thereof have been chosen for the purposes of illustration and description as shown in the accompanying drawings wherein:

Brief Description of the Drawings

FIG. 1 represents an isometric view of the blade carrier and strip guide and absent the presence of the plastic strip;

FIG. 2 represents a front view of the blade carrier of FIG. 1;

FIG. 3 represents a sectional view of the blade carrier with the view taken on the line 3—3 of FIG. 2 and looking in the direction of the arrows;

FIG. 4 represents a sectional view as in FIG. 3 and showing the blade carrier and the plastic strip and the leading grasping tongue of the plastic strip, the blade having separated a portion of skin from the body;

In the following description and in the claims details are identified by specific names for convenience. These names, however, are intended to be generic in their application. Corresponding reference characters refer to like members throughout the fourteen figures of the drawings.

Figure 7:
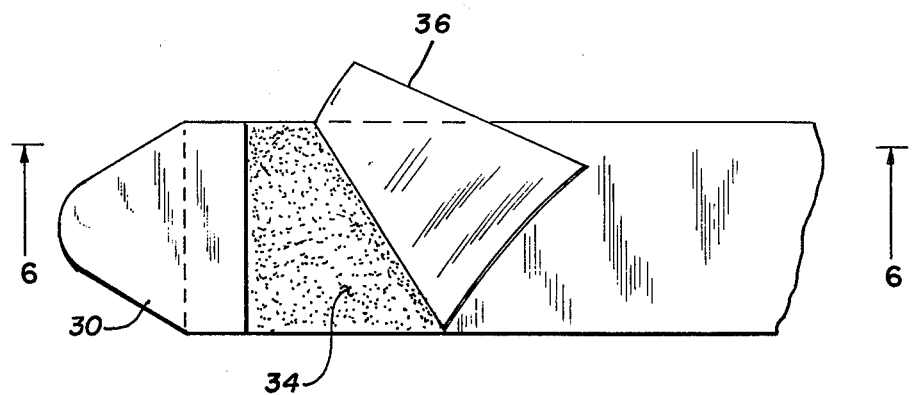
FIG. 7 represents a plan view, partly fragmentary, of a plastic strip and showing the tongue, the adhesively coated midportion and a release sheet partly removed from the adhesively coated surface.
Figure 6:
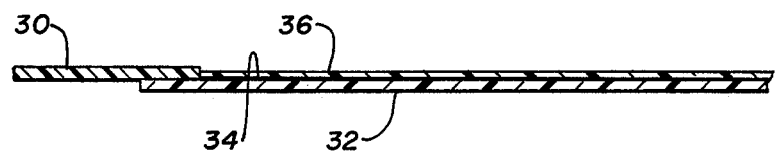
FIG. 6 represents a sectional side view of a plastic strip as used with the blade holder and showing a typical construction this view taken on the line 6—6 of FIG. 5 before the release sheet has been at least partially removed.

The drawings accompanying this specification disclose certain details of construction for the purpose of explanation but it is understood that they may be modified and that the expanding outer sleeve may be incorporated in other forms than shown.

DESCRIPTION OF THE EMBODIMENT OF FIGS. 1 THROUGH 7

Referring next to the drawings and in particular to FIGS. 1 through 7 wherein the simplest arrangement of the disposable dermatome is shown, this apparatus includes a blade holding member generally identified as 15. As particularly seen in FIGS. 3 and 4, this member 15 has a manipulating handle portion 16 which is generally adapted to be grasped by the user of the dermatome. End supports 17 and 18 carry and position a blade 19. This blade is preferably of sharpened steel similar to that of an injector razor blade. The blade is retained in upper and lower guide members 20 and 22 which may be of plastic and with the lower member 22 integral with end supports 17 and 18. The upper member 20 may be a force fit or secured by cement to the end supports on the lower member. However secured the blade 19 is positively retained.

The handle portion 16 and the blade 19, in combination with the upper and lower guides 20 and 22, provide a guideway 24 of a selected space or distance. A curve end 26 on the inner end of handle 16 provides a smooth surface for sliding on and over a plastic lift and guide strip member generally identified as 28. This strip member has a grasping tongue portion 30 which is tapered for entrance to and through guideway 24. This tongue is attached to or is a part of a midportion 32 which has the lower surface of this midportion coated with an adhesive surface 34. A release sheet or sheet portion 36 is placed on this adhesive portion until time for use. The width and length of the plastic strip midportion 32 and the adhesive portion thereof is the width and usually the length of skin to be removed. The thickness of midportion 32 in the guideway 24 between the cutting edge of blade 19 and the curved end 26 establishes the thickness of skin to be removed.

USE AND OPERATION

In use the surgeon or attendant who is to perform the skin removal prepares the skin surface selected in the usual manner. The midportion 32 of the plastic strip is cut or otherwise is selected as to the width and length. The thickness of the plastic strip 32 is also selected so as to provide a desired thickness of removed skin. The released sheet portion or portions 36, as shown in FIG. 7, are removed from the adhesive surface 34 and this exposed adhesive portin is placed on a body portion 38 (FIG. 4). The tongue portion 30 is guided through guideway 24 and with one hand grasping this tongue portion the holder 15 is moved back and forth in a reciprocating motion by the other hand to produce a cutting action by the blade 19. As seen in FIG. 4, this results in a thin portion of skin 40 which is cut from the body member 38 by the guided action of blade 18.

After cutting the desired area of skin, the plastic strip 28 with this removed skin is then severed from the patient and is transferred to the area to be treated. The removed skin and plastic may be cut into desired strips or the skin may be removed from the adhesive portion of the plastic strip and then tailored for application to the body area to be treated.

EMBODIMENT OF FIGS. 8 AND 9

Figure 8:
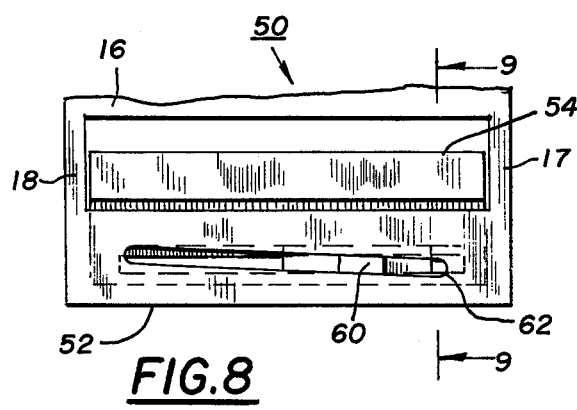
FIG. 8 represents a rear view, partly fragmentary, of an alternate blade holder in which the blade is selectively movable to various forward positions.
Figure 9:
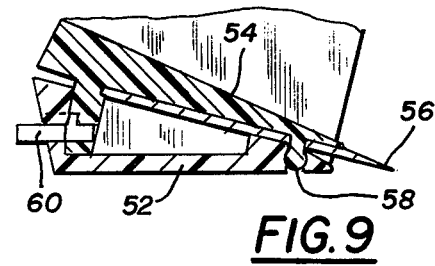
FIG. 9 represents a sectional view, in an enlarged scale, of the blade adjustable mechanism of FIG. 8, this view taken on the line 9—9 of FIG. 8 and looking in the direction of the arrows.
Figure 5:
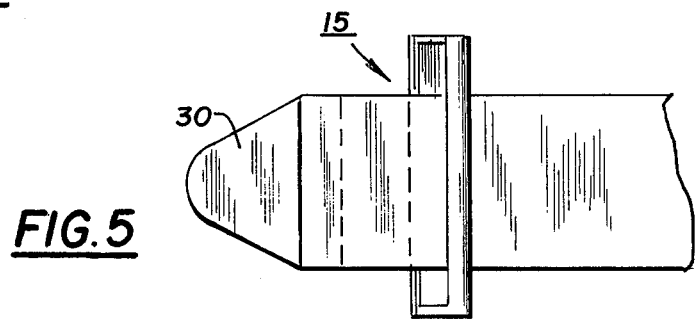
FIG. 5 represents a plan view, partly diagrammatic and in a reduced scale and showing the blade cutting holder and the plastic strip in an assembled condition and in use as in FIG. 4.

Referring next to FIGS. 8 and 9, there is shown an alternate blade holder on which the blade rather than in fixed position is movable within small limits into the guideway. This adjustment requires only one thickness of plastic while adjustment of the blade allows the thickness of the skin to be controlled by the forward extension of the cutting edge of the blade.

As shown, a holder generally identified as 50 is similar to holder 15 in that it has a handle portion 16 and end supports 17 and 18. A curved end 26 defines the handle side of the guideway 24. A lower guide member 52 is integrally attached to the end supports 17 and 18. An upper guide member 54 is retained by this lower member and is movable forwardly to the right, as seen in FIG. 9. A blade 56 is carried on a plurality of like pins or post members 58. A cam member 60 is carried in a slot 62 formed in member 52. Movement of the cam member 60 in slot 62 causes the blade edge to move up and down because of the slope of the slot 62 and, if desired, a small, formed portion on the inside of member 52 causes the cutting edge of blade 56 to move forwardly. This forward and up and down movement of the blade 56 into the guideway 24 causes an increase in the penetration of the blade into the skin. The thickness of skin removed is contemplated to be from 5 to 20 thousandths of an inch. Fifteen-thousandths of an inch of a forward movement of the blade 56 is thus contemplated.

ALTERNATE EMBODIMENT OF FIGS. 10 THROUGH 12

Figure 10:
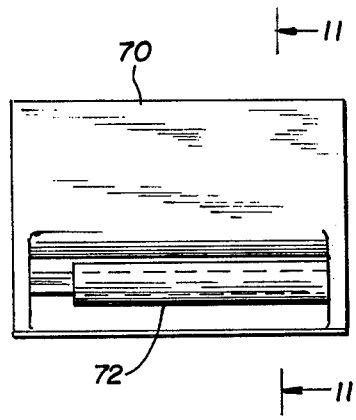
FIG. 10 represents a rear view of an alternate blade holder in which an oriented slide is provided to hold the blade in a desired relationship to a plastic strip guide.
Figure 11:
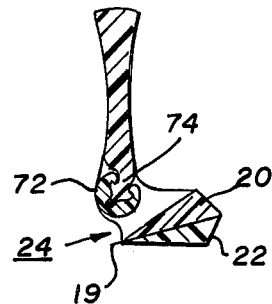
FIG. 11 represents a sectional view taken on the line 11—11 of FIG. 10 and looking in the direction of the arrows.
Figure 12:
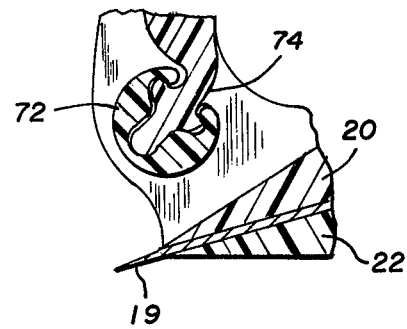
FIG. 12 represents in an enlarged scale a partly fragmentary sectional view showing in detail the slide guide depicted in FIG. 11.

Referring next to FIGS. 10, 11 and 12, there is shown an alternate blade holder assembly. In this arrangement the curved end is carried on a slide portion which is non-rotating. In this arrangement the guided plastic strip is held in place and down while the blade and holder are cycled back and forth. As shown, a handle portion 70 is secured to upper and lower guide portions 20 and 22. Blade 19 is retained between these guide portions. As shown, slide member 72 is slidable on a formed T-shaped guide portion 74 which is integral with the supports 17 and 18. The slide member 72 is more-or-less round and when positioned on the T-shaped guide 74 establishes the guideway 24. If desired, the blade may be made adjustable as in FIGS. 8 and 9.

EMBODIMENT OF FIGS. 13 THROUGH 15

Figure 13:
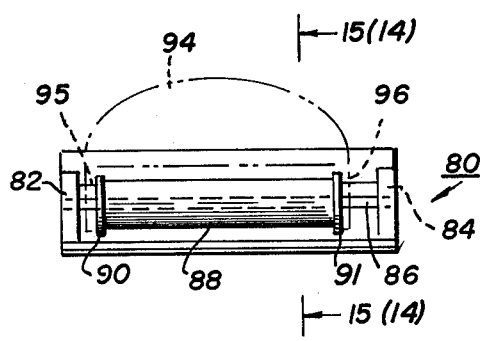
FIG. 13 represents a plan view of an alternate blade holder in which there is provided a rod slidably passing through a roller by which the plastic strip is guided and maintained against the skin of the patient.
Figure 14:
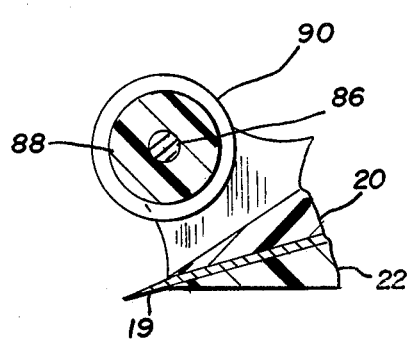
FIG. 14 represents a sectional view taken on the line 14—14 of FIG. 13 and looking in the direction of the arrows.
Figure 15:
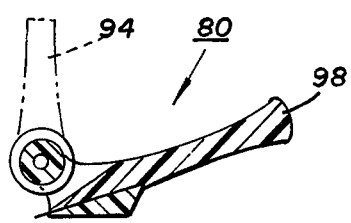
FIG. 15 represents a sectional view taken on the line 15—15 of FIG. 13 and looking in the direction of the arrows.

Referring next and finally to FIGS. 13, 14 and 15, there is shown a dermatome apparatus in which the curved end of the handle includes a free turning roller which is guided by the adhered plastic strip and which in turn guides the blade carrier and retained blade. As depicted, a blade holder 80 includes upper and lower guide members 20 and 22 and retained blade 19. Rather than the end supports 17 and 18 of FIGS. 1 through 4, there is provided rod support members 82 and 84 which support and carry the transverse rod portion 86. On this transverse rod 86 is slidably and rotatably carried a roller 88. Preferably this roller has end flange portions 90 and 91 which extend radially outwardly about the same amount as the thickness of the plastic strip midportion 32. The distance between flange portions is made to accommodate and slidably guide the plastic strip midportion 32. As an assist in holding the roller 88 to the skin and the plastic strip there may also be provided a guide handle 94 having fork ends 95 and 96 which are disposed adjacent the ends of the roller 88. These ends each have an aperture which is slidable on the rod 86. A handle or grip portion 98 is formed on holder 80 for convenience in grasping and moving the blade in a back and forth reciprocating motion to cut the skin at the desired thickness.

If desired, the guide handle 94 and its forked ends may be omitted as it is anticipated that the roller 88 will be held in place during cycling movement of the blade holder 80.

The above-described dermatome apparatus is adapted for one person operation and the use of inexpensive components anticipate the discarding after use. The size of the adhesively coated plastic strip determines the maximum area of skin to be removed with one plastic strip. More than one strip may be used, of course. If more than one strip is to be used, the strips may be applied as the blade holder is moved from one attached strip to the next. The removed skin may be kept with the strip until all the skin to be removed is on the several strips of adhesively coated plastic.

The several concepts of blade holder, above-described, are each disposed to be used with strips of plastic of determined thickness suck as 5 to 10 thousandths of an inch. The plastic strip has a given width and length to which adhesive is applied and also a re-leased sheet. Each strip has a grasping tongue which is tapered for ease of entry into a guideway in the blade holder. The strip of plastic may be cut to a smaller width and length, if desired. The thickness of skin cut from the body of the patient is directly related to the space in the guideway, the thickness of plastic strip and the positioning of the cutting edge of the blade from the curved surface forming one side of the guideway. The thickness of the plastic film strip and the cut skin is equal to this guideway space.

The above dermatome apparatus lends itself to a novel method in which the steps of removing a thin piece of skin of a given size from a body member utilizes this apparatus for achieving the needed steps. As a method the above apparatus, for a one-time use by the attendant or surgeon, includes the steps of providing a blade holder having a handle portion for grasping and moving the holder in and with a back and forth reciprocating motion; mounting and carrying a blade having a sharpened edge in and by said holder and with the blade movable with the holder as it is moved; forming a guideway in the blade holder and extending into this guideway the sharpened blade to define a determined spaced slot; forming a curved portion on an inner edge of the blade holder and defining a side of the guideway into which the blade enters; in combination with this blade holder there is also a forming and providing of a plastic strip including a tongue which is tapered to provide an easy entering portion into and through the guideway in the blade holder; this strip having a midportion of determined width, length and thickness; applying an adhesive surface to this midportion of the plastic strip and on one side thereof and providing thereby an adhesive attraction to that portion of skin to be removed, and placing a release sheet on the adhesive surface and providing therewith a protection for said adhesive surface until the release sheet is removed for placing the adhesive face of the strip on the skin to be removed, the cutting of and removal of the outer skin being accomplished by a back and forth reciprocating movement of the blade holder after threading the tongue of the plastic strip through the guideway of the blade holder and positioning the holder with the blade edge toward the adhered plastic strip and with a cutting by a reciprocating motion of the blade the plastic strip and thickness of adhered, severed skin is lifted from the body portion, the removed skin and adhered plastic strip is equal to the spaced slot in the guideway.

Terms such as "left," "right," "up," "down," "bottom," "top," "front," "back," "in," "out" and the like are applicable to the embodiments shown and described in conjunction with the drawings. These terms are merely for the purposes of description and do not necessarily apply to the position in which the dermatome apparatus and its portable plastic strips may be constructed or used.

While particular embodiments of the dermatome apparatus and method have been shown and described it is to be understood the invention is not limited thereto since modifications may be made within the scope of the accompanying claims and protection is sought to the broadest extent the prior art allows.

What is claimed is:

1. A dermatome apparatus combination adapted for a onetime use and operation by one person such as a surgeon or attendant for the removal of a selected area of skin of a determined thickness from a patient, this apparatus combination including: (a) a blade holder having a handle portion for assisting with grasping and moving the holder in and with a reciprocating motion; (b) a blade having a sharpened edge and carried in and by said holder and movable with the holder as it is moved, said reciprocating motion being parallel to said sharpened blade edge; (c) a guideway of a selected opening formed in the blade holder and with the sharpened edge of the blade projecting forwardly adjacent the bottom of the guideway to define a determined spaced opening; (d) a curved portion provided by the blade holder and defining a side of the guideway into which said cutting edge of the blade enters, the cutting edge of the blade being substantially parallel to the curved portion; (e) and in association and combination with said blade holder a plastic strip including a tongue end which is tapered to provide an easy entering portion into and through the guideway in the blade holder, the strip having a midportion of determined width, length and thickness, this width of the midportion being substantially less than the length of the guideway in the blade holder so that reciprocation of the blade holder can occur while the plastic strip is in the guideway; (f) an adhesive surface applied to this midportion of the plastic strip and on one side thereof to provide an adhesive attraction to that portion of skin to be removed by a cutting action of the blade, the plastic strip on that surface opposite the adhesive surface providing a slidable surface over and on which the curved portion slides, and (g) a release sheet applied to the adhesive surface and providing a protection for said adhesive surface until removed for placing the adhesive face of the strip on the skin to be removed from the patient whereby the cutting of and removal of the outer skin may be accomplished by a reciprocating movement of the blade holder and blade after threading the tongue of the plastic strip through the guideway of the blade holder and after pressing the adhesively coated portion of the strip to the skin of the patient with the holder positioned with the blade edge toward the adhered plastic strip on the skin and with the adhered skin lifted whereby a cutting motion of the blade allows the plastic strip and thickness of adhered, removed skin to be pulled through the guideway, the combination of the plastic strip and removed skin being of a thickness equal to the spaced opening in the guideway.

2. A dermatome apparatus combination as in claim 1 in which the blade as carried in the blade holder is adjustably carried in and by upper and lower guide members and is selectively movable between these guide members and into the guideway opening so as to control the width of the opening and the thickness of skin as it is cut by the blade, this adjustment of the blade permitting the thickness of the film to be preselected and unchanging while the penetration of the knife edge into the opening and skin is adjusted to suit the operator.

3. A dermatome apparatus combination as in claim 1 in which the blade is carried in and by upper and lower guide members with the ends of at least one of the guide members integrally attached to the blade holder.

4. A dermatome apparatus combination as in claim 1 in which the blade is carried by a retainer and guide member which has its ends attached to a slide guide and with a roller carried on this slide guide, this guide roller rotatable about the slide guide while the guide is slidable in the roller, this roller providing a determined spacing and attitude with the blade as it extends into the guideway opening.

5. A dermatome apparatus combination as in claim 4 in which the slide guide is a rod-like member which extends to and through the roller.

6. A dermatome apparatus combination as in claim 5 in which the roller has side guide portions by which and within which the film strip is guided as the skin is cut and lifted and there is provided an additional handle means including a fork portion with each of the fork portions disposed on each side of the roller and with the fork portions also slidable along the rod-like member.

7. A dermatome apparatus combination as in claim 1 in which the curved end portion of the blade holder is an arcuate member of a given length which is at least as long as the width of the strip of plastic and having a channel therethrough, this channel slidably retained on a male channel member carried by a lower guide member and providing a guide to retain and provide a slide support for the arcuate member.

8. A method for removing a thin layer of skin with the assist of an apparatus combination adapted for a one-time use and operation by one person such as a surgeon or attendant, the removal of a selected area of skin of a determined thickness from a patient through the use of a blade holder having a handle portion which is used to move the holder and a sharpened blade carried thereby, the holder having a guideway of a selected width and length and with the sharpened edge of the blade projecting forwardly adjacent the bottom of the guideway to define a determined spaced opening, the blade holder further having a curved portion on an inner edge, this curved portion being substantially parallel to the cutting edge and in association and combination with said blade holder forming and providing a plastic strip including a tongue which is tapered to provide an easy entering portion into and through the guideway in the blade holder, this strip having a midportion of determined width, length and thickness, this width of the midportion being substantially less than the length of the guideway opening in the blade holder, this strip having an adhesive surface on said midportion of the plastic strip and on one side thereof and providing therewith an adhesive attraction to that portion of skin to which it is pressed, the plastic strip on that surface opposite the adhesive surface providing a slidable surface, said plastic strip having a release sheet on the adhesive surface and providing therewith a protection for said adhesive surface until the release sheet is removed for placing the adhesive face of the strip on the skin to be removed from the patient, the cutting of and removal of the outer skin being accomplished by the steps of: (a) removing the release sheet from the adhesively coated side portion of the strip of plastic; (b) pressing the adhesively coated portion of the strip of plastic to that skin portion of the patient that is to be removed; (c) threading the tongue portion of the plastic strip through the guideway of the blade holder so that the outer surface is in sliding and guiding contact with the curved portion of the blade holder, and (d) cutting of and removal of the outer skin by reciprocating the blade holder in a motion parallel to the cutting edge of the blade so that the plastic strip and thickness of adhered, removed skin as a composite strip is pulled through the guideway, the combination of the plastic strip and removed skin being of a thickness equal to the spaced opening in the guideway.

9. A method of skin removal as in claim 8 which includes the further step of adjustably positioning the blade in the blade holder between upper and lower guide members and with said blade selectively movable between these guide members and into the guideway so as to control the width of the guideway and the thickness of skin as it is cut by the blade, this adjustment of the blade permitting the thickness of the plastic strip to be preselected and unchanging while the penetration of the knife edge into the guideway is adjusted to suit the operator.

10. A method of skin removal as in claim 8 which includes the further step of carrying the blade by a retainer and guide member which has its ends attached to a slide guide and carrying a roller on this slide guide, this guide roller rotatable about the slide guide while this guide is slidable in the roller, this roller providing a determined spacing and attitude with the blade as it expands into the guideway.

11. A method of skin removal as in claim 10 which includes the further step of forming on the roller side, guide portions by which and within which the plastic strip is guided as the skin is cut and lifted and there is provided an additional handle means including a fork portion with each of the fork portions disposed on each side of the roller and with the fork portions also slidable along the rod-like member.

* * * * *